(12) United States Patent
Chaplin et al.

(10) Patent No.: US 9,265,823 B2
(45) Date of Patent: *Feb. 23, 2016

(54) USE OF A MODIFIED POXVIRUS FOR THE RAPID INDUCTION OF IMMUNITY AGAINST A POXVIRUS OR OTHER INFECTIOUS AGENTS

(71) Applicant: BAVARIAN NORDIC A/S, Kvistgaard (DK)

(72) Inventors: Paul Chaplin, Gräfelfing (DE); Luis Mateo, Chapel Hill (AU)

(73) Assignee: BAVARIAN NORDIC A/S, Kvistgaard (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/328,474

(22) Filed: Jul. 10, 2014

(65) Prior Publication Data

US 2014/0341946 A1 Nov. 20, 2014

Related U.S. Application Data

(60) Continuation of application No. 13/335,097, filed on Dec. 22, 2011, now Pat. No. 8,808,709, which is a division of application No. 11/892,479, filed on Aug. 23, 2007, now abandoned, which is a continuation-in-part of application No. PCT/EP2006/001447, filed on Feb. 17, 2006.

(30) Foreign Application Priority Data

Feb. 23, 2005 (EP) ..................................... 05003873

(51) Int. Cl.
*A61K 39/285* (2006.01)
*C12N 15/86* (2006.01)
*A61K 39/12* (2006.01)
*A61K 39/00* (2006.01)

(52) U.S. Cl.
CPC ............... *A61K 39/285* (2013.01); *A61K 39/12* (2013.01); *C12N 15/86* (2013.01); *A61K 2039/5254* (2013.01); *A61K 2039/5256* (2013.01); *C12N 2710/24143* (2013.01)

(58) Field of Classification Search
None
See application file for complete search history.

(56) References Cited

U.S. PATENT DOCUMENTS

| | | | |
|---|---|---|---|
| 6,761,893 B2 | 7/2004 | Chaplin | |
| 7,097,842 B2 | 8/2006 | Suter | |
| 7,459,270 B2 | 12/2008 | Chaplin | |
| 8,268,327 B2 | 9/2012 | Hochrein | |
| 8,268,328 B2 | 9/2012 | Hochrein | |
| 8,808,709 B2 * | 8/2014 | Chaplin et al. ............. | 424/232.1 |
| 2002/0028195 A1 | 3/2002 | Coffey | |
| 2003/0202988 A1 * | 10/2003 | Chaplin et al. ............. | 424/232.1 |
| 2004/0175398 A1 | 9/2004 | Moyer | |
| 2004/0208850 A1 | 10/2004 | Ellenhorn | |
| 2010/0129404 A1 | 5/2010 | Hochrein et al. | |
| 2011/0177114 A1 | 7/2011 | Hochrein | |
| 2012/0107359 A1 | 5/2012 | Chaplin et al. | |

FOREIGN PATENT DOCUMENTS

| | | |
|---|---|---|
| WO | WO 03/088994 A2 | 10/2003 |
| WO | WO03097845 A1 | 11/2003 |
| WO | WO2004087201 A1 | 10/2004 |
| WO | WO2006089690 A1 | 8/2006 |

OTHER PUBLICATIONS

Kretzschmar et al. (Emerging Infectious Diseases. 2004; 10: 832-841).*
Vilsmeier (Berliner and Munchener Tierarztliche Wochenschrift. 1999; 112 (9): 329-333).*
Didierlaurent et al., Attenuated poxviruses expressing a synthetic HIV protein stimulate HLA-A2-restricted cytotoxic T-cell responses, Vaccine 22: 3395-3403, 2004.
Veryard et al., Interscience Conference on Antimicrobial Agents and Chemotherapy—44th Annul Meeting, !Drugs 7(12): 1055-1057, 2004.
Anon, Imvamune IND Receives Approval, Drug News Perspect. 17(5): 313, 2005.
Drexler et al., Modified vaccinia virus Ankara as antigen delivery system: how can we best use its potential?, Current Opinion in Biotechnology 15(6): 506-512, 2004.
Vollmar et al., 3rd Generation Smallpox Vaccine ImvarnuneTM (MVA-BN), Presented at the 2005 ASM Biodefense Meeting, Mar. 3, 2005.
Stittelar et al., Modified Vaccnia Virus Ankara Protects Macaques against Respiratory Challenge with Monkeypox Virus, Journal of Virology 79(12): 7845-7851, 2005.
Wyatt et al., Highly Attenuated smallpox vaccine protects mice with and without immune deficiencies against pathogenic vaccinia virus challenge, Proc. Natl. Acad. Sci. 101(13):4590-4595, 2004.
Stittelar et al., Antiviral Treatment is more effective than smallpox vaccination upon lethal monkeypox virus infection, Nature 439: 745-748 (2006).
Staib et al., Short-term, but not post-exposure, protection against lethal odhopoxvirus challenge after immnization with modified vaccinia virus Ankara, Journal of General Virology 87, 2917-2921, 2006.
Mortimer, Can Postexposure Vaccination against Smallpox Succeed?, Confronting Biological Weapons 36: 622-629, 2003.
Kretzschmar et al., Ring Vaccination and Smallpox Control, Emerging Infectious Diseases 10(5):832-842 (2004).
Vilsmeier, Paramunity-inducing effects of vaccinia strain MVA, Berl. Munch. Tierarztl. Wschr. 112: 329-333 (1999).
Report of Pretrial Re-examination for Japanese Application No. 2012-154752 dated May 1, 2015 (English Translation).

* cited by examiner

*Primary Examiner* — Shanon A Foley

(57) ABSTRACT

The present invention relates to the rapid induction of a protective immune response against infectious agents using a poxvirus. An immune response can be induced by administering the poxvirus 7 to 2 days prior to infection with the infections agents.

19 Claims, 6 Drawing Sheets

Figure 2

Challenge with 12.5x the $MLD_{50}$ of VV-WR

Vaccination (day relative to challenge)
- Saline control (Day -4)
- MVA-BN (Day -4)
- MVA-BN (Day -3)
- Dryvax (Day -4)
- Elstree-BN (Day -4)

USE OF A MODIFIED POXVIRUS FOR THE RAPID INDUCTION OF IMMUNITY AGAINST A POXVIRUS OR OTHER INFECTIOUS AGENTS

CROSS REFERENCE TO RELATED APPLICATIONS

This application is a continuation of application Ser. No. :13/335,097, filed on Dec. 22, 2011, now U.S. Pat. No. 8,808,709, which is a division of application No. 11/892,479, filed on Aug. 23, 2007, now abandoned, which is a continuation-in-part of application No. PCT/EP2006/001447, filed on Feb. 17, 2006, and claimed the benefit of EP05003873.3, filed on Feb. 23, 2005, all of which are incorporated by reference.

FIELD OF THE INVENTION

The present invention relates to the rapid induction of a protective immune response against poxviruses and poxvirus infections such as smallpox by vaccination of an animal, including a human, with a poxvirus that is replication incompetent in said animal, including the human. An example for such a poxvirus is a Modified Vaccinia virus Ankara (MVA). The invention further relates to the use of a recombinant poxvirus that is replication incompetent in the animal, including the human, that is vaccinated with the virus, such as a recombinant MVA expressing heterologous antigens and/or antigenic epitopes for a rapid induction of a protective immune responses against said heterologous antigen and/or antigenic epitope, e.g., against an antigen and/or antigenic epitope that is part of an infectious agent.

BACKGROUND OF THE INVENTION

For many diseases, such as infectious diseases, vaccines have been developed or are in the process of being developed. These vaccines induce a protective immune response within a certain time frame. Since most vaccines are used for the vaccination against diseases that are rather rare in the population, there is usually no need that the generation of the immune response be particularly rapid. However, there are situations in which an immune response, such as a protective immune response, should be generated as fast as possible. This may be the case in an outbreak of smallpox or in any other human poxvirus disease.

The causative agent of smallpox is the variola virus, a member of the genus Orthopoxvirus. Vaccinia virus, also a member of the genus Orthopoxvirus in the family of Poxviridae, was used as a live vaccine to immunize against smallpox. Successful worldwide vaccination with Vaccinia virus culminated in the eradication of variola virus (The global eradication of smallpox. Final report of the global commission for the certification of smallpox eradication; History of Public Health, No. 4, Geneva: World Health Organization, 1980). In the meantime, most of the stocks of infectious variola viruses have been destroyed. However, it can not be excluded that poxviruses, inducing smallpox or smallpox-like diseases, might again become a major health problem. In addition, there is a risk that a poxvirus disease of animals is spread to humans.

Moreover, there may also be other situations in which it is desirable to induce a rapid immune response. For example, it might be desirable to induce a rapid immune response against diseases that are endemic in some parts of the world, if it is necessary to travel to such a country at short notice.

BRIEF SUMMARY OF THE INVENTION

The invention encompasses the use of a poxvirus for the preparation of a vaccine for the rapid induction of a protective immune response in an animal, including a human, wherein the poxvirus is replication incompetent in said animal, including in the human.

In one embodiment, the invention encompasses a method for the rapid induction of a protective immune response in an animal, including a human, comprising the step of administering to the animal, including the human, a poxvirus that is replication incompetent in said animal, including in the human.

In one embodiment, the invention encompasses a use or method as above, wherein the protective immune response is generated within 7 days or less.

In one embodiment, the poxvirus is a Modified Vaccinia virus Ankara (MVA), particularly MVA 575, MVA 572 and, preferably, MVA-BN®.

The invention also encompasses uses or method as above, wherein the virus is a cloned, purified virus. Particularly the invention encompasses viruses obtained in a serum free cultivation process.

In one embodiment, the poxvirus is administered in a dose of $10^5$ to $5 \times 10^8$ TCID$_{50}$/ml. The poxvirus can be administered intravenously, intramuscularly or subcutaneously.

Preferably, the immune response is a protective immune response against a poxvirus infection, preferably, a smallpox infection.

In one embodiment, the poxvirus is a recombinant poxvirus, preferably a recombinant MVA-BN. The poxvirus can comprise at least one heterologous nucleic acid sequence. Preferably, the heterologous nucleic acid sequence is a sequence coding for at least one antigen, antigenic epitope, and/or a therapeutic compound. The antigenic epitopes and/or the antigens can be antigenic epitopes and/or antigens of an infectious agent. The infectious agents can be a viruses, fungi, pathogenic unicellular eukaryotic or prokaryotic organisms, and parasitic organisms. The viruses can be selected from the family of Influenza virus, Flavivirus, Paramyxovirus, Hepatitis virus, Human immunodeficiency virus, or from viruses causing hemorrhagic fever. The infectious agent can be *bacillus anthracis*.

The invention includes a method for inducing a immune response against an infectious agent in an animal comprising administering to the animal an immunogenic composition comprising an MVA, preferably MVA-BN, at 7 to 2, 6 to 2, 5 to 2, 4 to 2, 3 to 2, or any other combination of these days (i.e., 6 to 4, 6 to 3, 5 to 4, 5 to 3, etc.) prior to infection with an infectious agent. In one embodiment, the infectious agent is a replication competent poxvirus. In a preferred embodiment, the animal is a human.

The invention further encompasses uses of the above methods and kits comprising an immunogenic composition comprising an MVA, preferably MVA-BN, and instructions to deliver the immunogenic composition at a time point between 7 and 2 days prior to exposure to an infectious agent, including 7, 6, 5, 4, 3, or 2 days prior to exposure.

BRIEF DESCRIPTION OF THE DRAWINGS

FIG. 2. Changes in body weight of differently vaccinated mice following an intranasal challenge with 12.5× the MLD$_{50}$ of VV-WR. BALB/c mice were vaccinated subcutaneously with MVA-BN® or saline (PBS), or by scarification with Elstree, Dryvax®. Mice were treated with Saline (PBS) or Elstree, Dryvax 4 days, or with MVA-BN® 3 days prior to challenge with $4\times10^6$ TCID$_{50}$/ml, $1\times10^7$ TCID$_{50}$/ml, or $4\times10^7$ TCID$_{50}$/ml VV-WR per mouse. Body weight was measured prior to challenge (day 0) and then daily post challenge at the same time each day. The graph represents the average body weight changes per group over time using normalized (day 0 as baseline value) individual values.

DETAILED DESCRIPTION OF THE INVENTION

Figure 1:
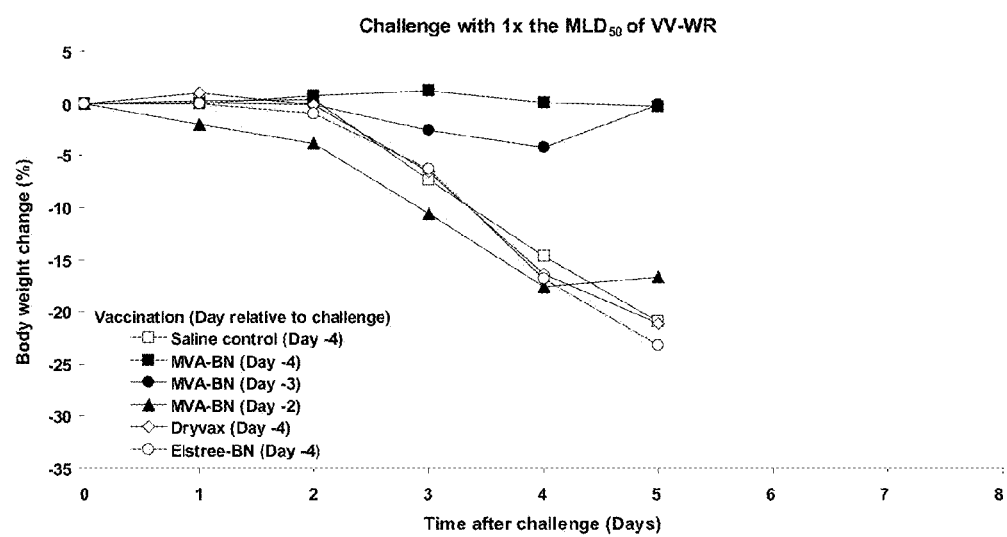
FIG. 1. Changes in body weight of differently vaccinated mice following an intranasal challenge with 1× the MLD$_{50}$ of VV-WR. BALB/c mice were vaccinated subcutaneously with MVA-BN® or saline (PBS), or by scarification with Elstree, Dryvax®. Mice were treated with Saline (PBS) or Elstree, Dryvax 4 days, or with MVA-BN® 3 days or 2 days prior to challenge with $4\times10^6$ TCID$_{50}$/ml, $1\times10^7$ TCID$_{50}$/ml, or $4\times10^7$ TCID$_{50}$/ml VV-WR per mouse. Body weight was measured prior to challenge (day 0) and then daily post challenge at the same time each day. The graph represents the average body weight changes per group over time using normalized (day 0 as baseline value) individual values.

The present invention relates to a method for the rapid induction of a protective immune response in an animal, including a human, comprising the step of administering to the animal, including the human, a poxvirus that is replication incompetent in said animal, including the human. The invention further relates to the use of said replication incompetent poxvirus for the preparation of a vaccine for the rapid induction of a protective immune response, as well as to a poxvirus as vaccine for the rapid induction of a protective immune response, wherein the poxvirus is replication incompetent in said animal, including the human.

The term "replication incompetent poxvirus" and the synonymous term virus that is "not capable of being replicated to infectious progeny virus" both refer to poxviruses that do not replicate at all in the cells of the vaccinated animal, and to viruses that show a minor residual replication activity that is controlled by the immune system of the animal, including the human, to which the poxvirus is administered.

According to an embodiment of the present invention, the replication incompetent poxviruses are viruses that are capable of infecting cells of the animal, including the human, in which the virus is used as vaccine. Viruses that are "capable of infecting cells" are viruses that are capable of interacting with the host cells to such an extent that the virus, or at least the viral genome, becomes incorporated into the host cell. Although the viruses used according to the present invention are capable of infecting cells of the vaccinated animal, including a human, they are either not capable of being replicated to infectious progeny virus in the cells of the vaccinated animal, or they show only a minor residual replication activity that is controlled by the immune system of the animal, including the human, to which the poxvirus is administered.

It is to be understood that, a virus that is capable of infecting cells of a first animal species but not capable of being replicated to infectious progeny virus in said cells may behave differently in a second animal species. For example, for humans, MVA-BN® and its derivatives (see below) are viruses that are capable of infecting cells of the human but that are not capable of being replicated to infectious progeny virus in human cells. The same viruses are very efficiently replicated in chickens; i.e. in chickens, MVA-BN® is a virus that is capable of infecting cells and capable of being replicated to infectious progeny virus. It is known to the person skilled in the art which virus has to be chosen for a specific animal species. A test that allows determining whether a virus is capable or not capable of being replicated in severely immunocompromised mice is disclosed in WO 02/42480 and uses the AGR129 mice strain (see below), or any other mouse strain that is incapable of producing mature B and T cells and as such is severely immune compromised and highly susceptible to a replicating virus. The results obtained in this mouse model are indicative for humans.

Some MVAs, such as MVA-572 and MVA-575, are not as attenuated as MVA-BN, as elucidated in WO 02/42480. For example, MVA-572 is capable of killing severely immunocompromised mice.

According to an embodiment of the present invention, the viruses according to the present invention are capable of being replicated in at least one type of cells of at least one animal species. Thus, it is possible to amplify the virus prior to administration to the animal that is to be vaccinated and/or treated. By way of example, reference is made to MVA-BN® that can be amplified in CEF (chicken embryo fibroblasts) cells but that is a virus that is not capable of being replicated to infectious progeny virus in humans.

According to an embodiment of the present invention, Modified Vaccinia virus Ankara (MVA) is used in humans and several animal species, such as mice and non-human primates. MVA is known to be exceptionally safe. MVA has been generated by long-term serial passages of the Ankara strain of Vaccinia virus (CVA) on chicken embryo fibroblasts (for review see Mayr, A., Hochstein-Mintzel, V. and Stickl, H. [1975] Infection 3, 6-14; Swiss Patent No. 568, 392). Examples for MVA virus strains that have been deposited in compliance with the requirements of the Budapest Treaty and that are useful in the practice of the present invention are strains MVA 572 deposited at the European Collection of Animal Cell Cultures (ECACC), Salisbury (UK) with the deposition number ECACC 94012707 on Jan. 27, 1994, MVA 575 deposited under ECACC 00120707 on Dec. 7, 2000, and MVA-BN® deposited with the number 00083008 at the ECACC on Aug. 30, 2000. Although MVA-BN is preferred to its higher safety (less replication competent), all MVAs are suitable for this invention.

According to an embodiment of the present invention, the MVA strain is MVA-BN® and its derivatives. A definition of MVA-BN® and its derivatives is given in PCT/EP01/13628.

In short, MVA-BN® and its derivatives as disclosed in PCT/EP01/13628 are characterized in having at least one, at least two, at least three or all of the following properties:
(i) capability of reproductive replication in chicken embryo fibroblasts (CEF) and in the cell line BHK, but no capability of reproductive replication in human cell lines. According to an embodiment of the present invention the human cell lines are the human bone osteosarcoma cell line 143B, the human keratinocyte cell line HaCat and the human cervix adenocarcinoma cell line HeLa,
(ii) failure to replicate in vivo in severely immune compromised mice,
(iii) induction of a higher immunogenicity compared to the known strain MVA 575 (ECACC V00120707) in a lethal challenge model and/or
(iv) induction of at least substantially the same level of immunity in vaccinia virus prime/vaccinia virus boost regimes when compared to DNA-prime/vaccinia virus boost regimes.

For detailed information regarding the assays used to determine whether a MVA strain has one or more of the above features (i) to (iv) reference is made to WO 02/42480 (PCT/EP01/13628). This publication also discloses how viruses having the desired properties can be obtained. In the following it is shortly summarized how the person skilled in the art can test whether an MVA strain has one or more of said features and is, thus, a virus according to said embodiment of the present invention. The following summary is not to be understood as to limit the relevance of WO 02/42480 for the present application to the following information. Instead, WO 02/42480 is herewith incorporated in its entirety by reference.

The term "not capable of reproductive replication" in human cell lines such as the cell lines HaCAT (Boukamp et al. 1988, J Cell Biol 106(3): 761-71) or HeLa is used in the present application as defined in WO 02/42480. Thus, a virus that is "not capable of reproductive replication" in a cell line is a virus that shows an amplification ratio of less than 1 in said cell line. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells. According to an embodiment of the present invention the viruses that are "not capable of reproductive replication" in human cell lines may have an amplification ratio of 1.0 (average value) or less, or even 0.8 (average value) or less, in any of the above human cell lines HeLa, HaCat and 143B.

The term "average" as used in the present application refers to the average values obtained from at least 2, but possibly 3, 4, 5, 6, 7, 8, 9, 10 or more experiments. It will be understood by a person skilled in the art that single experiments may deviate from average values due to the inherent variability of biological systems.

The term "failure to replicate in vivo" is used in the present application as defined in WO 02/42480. Thus, said term refers to viruses that do not replicate in the mouse model as explained in WO 02/42480. The mice used in WO 02/42480 are incapable of producing mature B- and T-cells (AGR 129 mice). MVA-BN® and its derivatives do not kill AGR129 mice within an average time period of at least 45 days (average value), such as within at least 60 days (average value), or within 90 days (average value) after the infection of the mice with $10^7$ pfu virus administered intraperitoneally. According to an embodiment of the present invention, the viruses that show "failure to replicate in vivo" are further characterized in that no virus can be recovered from organs or tissues of the AGR129 mice 45 days (average value), alternatively 60 days (average value), and alternatively 90 days (average value), after the infection of the mice with $10^7$ pfu virus administered intraperitoneally. Instead of the AGR129 mice, any other mouse strain can be used that is incapable of producing mature B and T cells, and as such is severely immune compromised and highly susceptible to a replicating virus. The data obtained in said mouse model are predictive for humans. Thus, according to an embodiment, the viruses of the present invention, such as MVA-BN® and its derivatives, do not replicate at all in humans. In applying the definition in the section related to the terms "replication incompetent poxvirus" and "virus that is not capable of being replicated to infectious progeny virus" to the replication behavior of MVA-BN® and its derivatives in humans, additional viruses that are within the scope of the present invention are those that show a minor residual replication activity that is controlled by the immune system of the human to which the poxvirus is administered.

The details of the lethal challenge experiment used to determine whether an MVA strain has "a higher immunogenicity compared to the known strain MVA 575" are explained in WO 02/42480. In such a lethal challenge model, unvaccinated mice die after the infection with replication competent vaccinia strains, such as the Western Reserve strain L929 TK+ and IHD-J. The infection with replication competent vaccinia viruses is referred to as "challenge" in the context of description of the lethal challenge model. Four days after the challenge, the mice are usually killed and the viral titer in the ovaries is determined by standard plaque assays using VERO cells. The viral titer is determined for unvaccinated mice and for mice vaccinated with MVA-BN® and its derivatives. More specifically MVA-BN® and its derivatives are characterized in that, in this test, after the vaccination with $10^2$ $TCID_{50}$/ml virus, the ovary virus titers are reduced by at least 70% (average value), alternatively by at least 80% (average value), alternatively by at least 90% (average value), compared to unvaccinated mice.

A vaccinia virus, such as an MVA strain, is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in WO 02/42480 is at least substantially the same in vaccinia virus prime/vaccinia virus boost regimes when compared to DNA-prime/vaccinia virus boost regimes. According to an embodiment of the present invention, the CTL response is at least substantially the same in vaccinia virus prime/vaccinia virus boost regimes when compared to DNA-prime/vaccinia virus boost regimes as measured in both of the "assay 1" and "assay 2" as disclosed in WO 02/42480. According to an embodiment of the present invention, the CTL response after vaccinia virus prime/vaccinia virus boost administration is higher in at least one of the assays, when compared to DNA-prime/vaccinia virus boost regimes. According to an embodiment of the present invention the CTL response is higher in both assays.

According to an embodiment of the present invention, the derivatives of MVA-BN® are characterized (i) in being capable of reproductive replication in chicken embryo fibroblasts (CEF) and in the Baby hamster kidney cell line BHK, but not capable of reproductive replication in human cell lines, wherein according to an embodiment of the present invention the human cell lines are the human bone osteosarcoma cell line 143B, the human keratinocyte cell line HaCat and the human cervix adenocarcinoma cell line HeLa; and (ii) by a failure to replicate in vivo in severely immune compromised mice.

According to an embodiment of the present invention, the virus is a cloned purified virus, such as a monoclonal virus.

According to an embodiment of the present invention, the virus is a virus that has been produced/passaged under serum free conditions to reduce the risk of infections with agents contained in serum.

MVA according to the present invention is administered in a concentration range of $10^4$ to $10^9$ TCID50/ml, e.g. in a concentration range of e.g. $10^5$ to $5 \times 10^8$ $TCID_{50}$/ml or in a concentration range of e.g. $10^6$ to $10^8$ $TCID_{50}$/ml. The actual concentration depends on the type of the virus and the animal species to be vaccinated. For MVA-BN® a typical vaccination dose for humans comprises $5 \times 10^7$ $TCID_{50}$ to $5 \times 10^8$ $TCID_{50}$, e.g. about $1 \times 10^8$ $TCID_{50}$, administered subcutaneously.

According to an embodiment of the present invention, the poxvirus as defined above, e.g. an MVA strain, such as MVA-BN® and its derivatives is administered in a single administration to induce a rapid protective immune response. Clinical data have shown that a single vaccination with MVA-BN® resulted in a detectable immune response in almost 100% of the vaccinated individuals.

According to another embodiment of the present invention the poxvirus as defined above, e.g. an MVA strain, such as MVA-BN® and its derivatives may also be used in homologous prime boost regimes. In other words, it is possible to use a poxvirus such as MVA for a first vaccination and to boost the immune response generated in the first vaccination by administration of the same or a related strain of the poxvirus than the one used in the first vaccination. The poxvirus as defined above, e.g. an MVA strain, such as MVA-BN® and its derivatives may also be used in heterologous prime-boost regimes in which one or more of the vaccinations is done with a poxvirus as defined above and in with one or more of the vaccinations is done with another type of vaccine, e.g. another virus vaccine, a protein or a nucleic acid vaccine.

The mode of administration may be intravenously, intradermal, intranasal, or subcutaneously. Any other mode of administration may be used.

The poxvirus used according to the present invention may be a non-recombinant poxvirus such as an MVA strain, e.g. MVA-BN® and its derivatives. In this case, the vaccination may be done to rapidly induce a protective immune response against a poxvirus infection such as smallpox.

Thus, according to the present invention, the poxvirus as defined above, such as an MVA strain, e.g. MVA-BN® and its derivatives is suitable to rapidly induce a protective immune response against smallpox. This is exemplified in Example 1, where it is compared how long it takes until a protective immune response is generated in mice against a pathogenic vaccinia virus strain, after vaccination with MVA-BN® (a strain according to the present invention) and with non-MVA strains such as Dryvax® and Elstree. These non-MVA strains are fully replication-competent, in contrast to MVA-BN®. It is shown that MVA-BN® clearly has improved properties compared to Elstee and Dyvax, in that a single vaccination of mice with MVA-BN® leads to a significant protective immune response, when the vaccination is administered within four, three and even two days before exposure to the pathogenic vaccinia virus strain. For example, this is demonstrated by assessing, in the mice's lungs, the titer of a pathogenic Vaccinia virus strain Western reserve (VV-WR) administered to a mouse two, three or four days after the vaccination with MVA-BN®. When the mice were challenged with 12.5× $MLD_{50}$ of VV-WR three days after the vaccination, no VV-WR viral titer could be detected in mice vaccinated with a standard dose of MVA-BN®, whereas the mice vaccinated with Dryvax® or Elstree were not protected and had a lung titer that was very similar to the titer of unvaccinated control mice. When the mice were challenged with 50×$MLD_{50}$ four days after the vaccination, no VV-WR viral titer could be detected in mice vaccinated with a standard dose of MVA-BN®, whereas the mice vaccinated with Dryvax® or Elstree were not protected and had a lung titer that was very similar to the titer of unvaccinated control mice. The term $MLD_{50}$ refers to the concentration of a pathogenic Vaccinia virus strain at which 50% of the inoculated mice die.

It is to be noted that the mice data are predictive for humans. Moreover, it is to be taken into account that concentrations of a pathogenic virus that are 50 times the lethal dose usually do not occur in nature, in particular not for human poxviruses that induce smallpox.

According to an embodiment of the present invention, the term "rapid induction of a protective immune response in an animal, including a human" refers preferably to the generation of a protective immune response within 7 days or less, 6 days or less, 5 days or less, 4 days or less, 3 days or less, or even 2 days or less, after the vaccination with a virus according to the present invention. This is unexpected since it was a dogma in the state of the art that it takes at least 10 to 14 days until a protective immune response is generated against traditional smallpox vaccines, based on replicating vaccinia virus strains. The rapidity of the induction of a protective immune response can be evaluated in the animal model described in the examples section. Said model is also predictive for humans. Thus, according to an embodiment of the present invention a poxvirus vaccine is effective in inducing a rapid immune response in mice if after vaccination of mice with an effective dose of a poxvirus vaccine such as MVA, e.g. MVA-BN® and derivatives thereof, and challenge with 1×, 12.5×, and 50×$MLD_{50}$ of VV-WR four days after vaccination, the lung titers of the virus are below an average of $5 \times 10^3$ pfu (corresponding to log 3.69), as determined in the test system described in the examples section. Alternatively, according to an embodiment of the present invention, a poxvirus vaccine is effective in inducing a rapid immune response if the lung titer values are below an average of $5 \times 10^3$ pfu (corresponding to log 3.69) after a challenge with 1×, and 12.5×$MLD_{50}$ of VV-WR three days after vaccination with an effective dose of the poxvirus vaccine.

In a broader sense, a virus leads to a rapid induction of a protective immune response in mice if said virus behaves similarly to MVA-BN® in the lung titer assay and the body weight assay described in the examples section. Thus, the limits, threshold values, conditions and parameters as described in the examples section, also apply in a general sense for other poxvirus vaccines that are regarded as rapid inducers of a protective immune response. From this, it is obvious that the data and information given in the examples section can be generally used to supplement any missing data and information in this paragraph, such as information relating to the description of the test system.

Alternatively, the rapidity of the induction of the protective immune response can be evaluated with the serum conversion test explained below; in this context, the time point at which seroconversion is observed is regarded as the time point at which the protective immune response was induced.

According to an embodiment of the present invention the animal, including a human, is an animal that is naïve with respect to poxvirus infections, i.e. an animal that has never been in contact with poxviruses and that has not been vaccinated with poxvirus vaccines.

According to a related embodiment the animal, including a human, is an animal that was in contact with poxviruses and/or that was vaccinated with a poxvirus vaccine. Such animal, including a human, might have raised an immune response against poxviruses and/or poxvirus vaccines, such as MVA.

The term "protective immune response" means that the vaccinated animal is able to control an infection with the pathogenic agent against which the vaccination was done. Usually, the animal having developed a "protective immune response" develops only mild to moderate clinical symptoms or no symptoms at all. Usually, an animal having a "protective immune response" against a certain agent will not die as a result of the infection with said agent.

As pointed out above, a concentration of MVA-BN® or a derivative thereof used for the generation of a protective immune response in humans against smallpox is in the range of $5 \times 10^7$ TCID$_{50}$ to $5 \times 10^8$ TCID$_{50}$, such as $1 \times 10^8$ TCID$_{50}$, wherein the virus may be administered subcutaneously or intramuscularly.

It seems as if the mechanism of the development of a rapid immune protection after vaccination with a poxvirus as defined above, such as an MVA strain, e.g. MVA-BN® and its derivatives, depends on whether the vaccinated animal, including a human, is a naïve animal (that was never in contact with a poxvirus before) or an animal that had been in contact with a poxvirus before (e.g. by vaccination). In the naïve animal, including a human, the administration of the poxvirus according to the present invention, such as MVA-BN® or its derivatives efficiently primes the immune system, even if neutralizing antibodies may not be detectable in the first few days after vaccination (see Example 2). The infection with a pathogenic virus boosts the immune system, in such way that the effectively primed immune system can control said infection unexpectedly effective and fast (see Example 2). Thus, naïve animals that have been vaccinated with a virus according to the present invention are readily protected against the infection with the pathogenic virus against which the vaccination is done after a single vaccination only.

The viruses as defined according to the present invention, such as MVA-BN® and its derivatives also are unexpectedly efficient and fast in boosting the earlier vaccination in animals that have been in contact with a poxvirus before, so that a protective immune response is also rapidly generated in this situation.

The rapidity of the induction of a protective immune response is also reflected by an unexpectedly fast seroconversion after vaccination of animals, including humans, with a virus according to the present invention such as MVA, e.g. MVA-BN® and its derivatives. In non-human primates, it is shown that seroconversion occurs within less than 10 days, e.g. within 7 days, which is one week faster than the seroconversion after vaccination with other smallpox vaccines, such as Elstree. In the following it is described how the seroconversion after vaccination with MVA-BN® and its derivatives is evaluated. The same test principle is applied mutatis mutandis if the seroconversion after vaccination with other viruses is tested. The only modification that is required to assess the seroconversion induced by said other viruses is to quantify the total IgG antibodies specific for said other viruses, instead of quantifying the total MVA-BN® specific IgG antibodies. The cut off values and the criteria to evaluate whether a sample is positive are determined in basically the same way, with optional minor modifications that are within the skills of the skilled artisan. To assess for a seroconversion after vaccination with MVA-BN® (or its derivatives), total MVA-BN® specific IgG antibodies are quantified in test sera using a direct Enzyme-Linked Immunosorbent Assay (ELISA). A detailed description of a study applying this method is provided in Example 2.

The ELISA is a sensitive method used for the detection of antibodies in sera. The MVA-BN® specific ELISA is a standard binding ELISA used to detect total IgG antibodies in human test sera. ELISA results are expressed as an end point antibody titer obtained by direct determination of logarithmic trend lines. A cut off, or end point absorbance of 0.35 has been defined. The end point titer of the sample is determined by generating a logarithmic plot, e.g. by using the commercially available computer program Excel (expressing optical density (OD) on the y axis and the log of the sera dilution on the x axis). Again, the data in non-human primates are predictive for humans. A test sample is deemed positive when the OD of the sample is greater than 0.35 at a 1:50 dilution of a test sample. The geometric mean titer (GMT) is calculated by taking the antilogarithm of the mean of the log 10 titer transformations. The GMT is usually the reported titer for ELISA titers.

Seroconversion rate is defined as percentage of initially seronegative subjects with appearance of antibody titers≥1:50 in the MVA-specific IgG ELISA. Thus, according to an embodiment of the present invention the term "rapid induction of a protective immune response in an animal, including a human" refers to a seroconversion as defined above, with the test as defined above, within 10 days or less, 7 days or less, 6 days or less, 5 days or less, 4 days or less, 3 days or less, or even 2 days or less, after the vaccination with a virus according to the present invention.

The poxvirus as defined above such as an MVA strain, e.g. MVA-BN® and its derivatives may also be a recombinant poxvirus strain such as recombinant MVA-BN® or its derivatives. The recombinant viruses according to the present invention, such as recombinant MVA-BN® and its derivatives, may contain at least one heterologous nucleic acid sequence. The term "heterologous" is used hereinafter for any combination of nucleic acid sequences that is not normally found intimately associated with the virus in nature. The heterologous sequences may be antigenic epitopes or antigens, which are selected from any non-vaccinia source. According to an embodiment of the present invention, said recombinant virus expresses one or more antigenic epitopes or antigens, which are antigenic epitopes or antigens from an infectious agent. The infectious agent may be any infectious agent, such as a virus, a fungus, a pathogenic unicellular eukaryotic or prokaryotic organism, and a parasitic organism. Examples of infectious agents are Plasmodium falciparum, Mycobacteria, Influenza virus, Flaviviruses, Paramyxoviruses, Hepatitis viruses, Human immunodeficiency viruses, viruses causing hemorrhagic fever such as Hantaviruses or Filoviruses, i.e., Ebola and Marburg virus. The infectious agent can be *bacillus anthracis*, which causes anthrax.

According to this embodiment the recombinant poxvirus as defined above may not only be used to induce a rapid immune response against a poxvirus infection, but may also (or alternatively) be used to induce a rapid immune response against the heterologous antigenic epitope/antigen expressed from the heterologous nucleic acid comprised in the recombinant virus. Thus, by way of example, if a recombinant MVA expresses an HIV epitope or a yellow fever virus epitope, the recombinant MVA may be used to induce a rapid immune response against HIV or Yellow fever virus, respectively.

It is also within the scope of the present invention that the recombinant virus may alternatively express an antigenic epitope/antigen that further increases the immunogenicity of MVA.

The recombinant virus used according to the present invention may also comprise a heterologous gene/nucleic acid expressing a therapeutic compound. A "therapeutic compound" encoded by the heterologous nucleic acid in the virus can be, for example, a therapeutic nucleic acid such as an antisense nucleic acid, or a peptide, or a protein with desired biological activity.

According to an embodiment of the present invention, the expression of heterologous nucleic acid sequence may be under the transcriptional control of a poxvirus promoter. An example of a suitable poxvirus promoter is the cowpox ATI promoter (see WO 03/097844).

According to an embodiment of the present invention, the insertion of a heterologous nucleic acid sequence is done into a non-essential region of the virus genome. According to another embodiment of the invention, the heterologous nucleic acid sequence is inserted at a naturally occurring deletion site of the MVA genome (disclosed in PCT/EP96/02926). According to a further alternative, the heterologous sequence may be inserted into an intergenic region of the poxviral genome (see WO 03/097845). Methods on how to insert heterologous sequences into the poxviral genome are known to a person skilled in the art.

The invention also encompasses kits for the induction of a protective immune response. In one embodiment, the kit comprises an immunogenic composition comprising an MVA and instructions for the delivery of the immunogenic composition. The MVA is preferably MVA-BN. Preferably, the immunogenic composition contains $10^5$ to $5 \times 10^8$ TCID$_{50}$/ml of MVA. The instructions for delivery of the immunogenic composition can direct the delivery at various time points prior to exposure to an infectious agent. These time points can include time points between 7 and 2 days prior to exposure to an infectious agent. In this context, an "exposure" means contact with the infectious agent itself, or with an animal (human) harboring the infectious agent. The time points can also include time points between 6 and 2 days, 5 and 2 days, 4 and 2 days, 3 and 2 days, and 2 days prior to exposure to an infectious agent. For example, the instructions can direct that the immunogenic composition can be delivered at 7, 6, 5, 4, 3, or 2 days prior to exposure to an infectious agent. Preferably, the infectious agent is smallpox or *bacillus anthracis*. The instructions can direct that the MVA be administered MVA intravenously, intramuscularly, and/or subcutaneously.

All definitions given above for the embodiment regarding non-recombinant viruses apply also for the embodiment concerning recombinant viruses.

The specification is most thoroughly understood in light of the cited references, all of which are hereby incorporated by reference in their entireties.

EXAMPLES

The following examples will further illustrate the present invention. It will be well understood by a person skilled in the art that the provided examples in no way may be interpreted in a way that limits the applicability of the technology provided by the present invention to this examples.

Example 1

Onset of Protection in MVA-BN®, Elstree, or Dryvax® Vaccinated Mice Challenged with 1×, 12.5×, or 50× the MLD$_{50}$ of Vaccinia Virus VV-Western Reserve (VV-WR) on Days 2 Through 4 Post-Vaccination: Assessment by Body Weight and Lung Titers 1. Introduction A murine intranasal vaccinia challenge model has been developed to test the efficacy of smallpox vaccine candidates. In this model, mice are vaccinated with vaccines the efficiency of which is to be determined. Control mice receive a saline control instead of the vaccine. Several days after the vaccination, the mice are infected with a pathogenic Vaccinia virus strain, such as the vaccinia virus strain Western Reserve (VV-WR). The murine lethal dose 50 (MLD$_{50}$) of the vaccinia virus strain Western Reserve (VV-WR) was determined to be $3.6 \times 10^4$ TCID$_{50}$ in unvaccinated mice.

In a preliminary study it was shown that MVA-BN®-vaccinated BALB/c mice challenged with either 25× or 50× the MLD$_{50}$ of VV-WR, quickly recovered from the viral challenge, showed no clear signs of clinical symptoms, and no pathological lesions were present in the lungs of these animals. In another preliminary study, the time required after vaccination to establish protection from a lethal challenge with VV-WR was investigated: challenging of MVA-BN®-vaccinated mice with a sub-lethal dose of VV-WR 3 days after the vaccination, revealed protection (with regard to body weight loss and viral lung titers). The objective of this example was to narrow down the time required after MVA-BN® (or Elstree or Dryvax®) vaccination to obtain protection following a lethal challenge with VV-WR.

2. Viruses and Controls

Test Vaccine 1

Modified Vaccinia Ankara-Bavarian Nordic (MVA-BN®/IMVAMUNE®), in a concentration of 5.0E+08 TCID$_{50}$/ml. Formulation: in 10 mM Tris 140 mM NaCl pH7.4.

No further dilutions of the MVA-BN® stock were made in the MVA-BN® vaccinated groups and 200 µl was administered subcutaneously, resulting in a final dose of 1.0E+08 TCID$_{50}$.

Test Vaccine 2

Vaccinia virus strain Elstree with a nominal concentration of 1.0E+08 TCID$_{50}$/ml. Formulation: in 10 mM Tris 140 mM NaCl pH7.4.

No further dilutions of the Elstree stock were made and 2.5 µl was administered via scarification on the tail of each mouse, resulting in a final dose of 2.5E+05 TCID$_{50}$.

Test Vaccine 3

Dryvax® with a nominal concentration of 2.9E+07 TCID$_{50}$/ml. Formulation: in 10 mM Tris 140 mM NaCl pH7.4.

No further dilutions of the Dryvax® stock were made and 8 µl was administered via scarification on the tail of each mouse, resulting in a final dose of 2.5E+05 TCID$_{50}$.

Each of the test vaccines 1 to 3 was administered with its optimal dose and route of administration.

Challenge Virus

Vaccinia Virus Western Reserve (VV-WR) with a nominal concentration of 4.0E+08 TCID$_{50}$/ml.

The following dilutions of VV-WR (4.0E+08 TCID$_{50}$/ml) were made to generate a final working stock of 8.0E+05 TCID$_{50}$/ml and 4.0E+07 TCID$_{50}$/ml: For 1× the MLD$_{50}$ of VV-WR/mouse (8.0E+05 TCID$_{50}$/ml working stock suspension): 100 µl of the VV-WR stock 4.0E+08 TCID$_{50}$/ml was added to 900 µl of PBS, mixed by vortexing (to give a concentration of 4.0E+07 TCID$_{50}$/ml); 100 µl of this suspension was transferred to 900 µl of PBS, again mixed by vortexing (to give a concentration of 4.0E+06 TCID$_{50}$/ml); 600 µl of this suspension was added to 2400 µl of PBS, mixed by vortexing to give a final concentration of 8.0E+05 TCID$_{50}$/ml. For 12.5× the MLD$_{50}$ of VV-WR/mouse (1×107 TCID50/ml working stock suspension): 75 µl of the VV-WR stock 4×108 TCID50/ml was added to 2925 µl of PBS and mixed by vortexing to give a final concentration of 1×107 TCID50/ml. For 50× the MLD$_{50}$ of VV-WR/mouse (4.0E+07 TCID$_{50}$/ml working stock suspension): 300 µl of the VV-WR stock 4.0E+08 TCID$_{50}$/ml was added to 2700 µl of PBS and mixed by vortexing to give a final concentration of 4.0E+07 TCID$_{50}$/ml.

Saline Control:

In the Saline Control groups, 200 µl PBS (as supplied by the manufacturer) was used for injecting individual mice subcutaneously 3. Methods and Experimental Design Test System Specific Pathogen Free (SPF) female Balb/c mice H-2d were obtained from Taconic M&B, P.O. Box 1079, DK-8680 Ry, Denmark. Number of animals in the study: 60. Age at initiation of challenge: 9 weeks. Body weight range at initiation of challenge: 18-23 grams. The BALB/c mouse strain has been used extensively to test the immunogenicity and efficacy of smallpox vaccines. The strain is highly susceptible to VV-WR challenge.

The experiments were carried out in accordance with the Dyreforsøgstilsynet of Denmark Allocation to treatment groups: On arrival, animals were randomly allocated to a treatment group consisting of 5 animals per test group (and cage).

Justification of the dose level: MVA-BN® was used at an optimal dose that has been demonstrated in previous experiments to induce strong humoral and cell mediated immune responses in mice. Elstree and Dryvax® were used at a dose suggested for humans.

Vaccination and Challenge Schedule

A total of 80 mice were used in this study (see Table 1 below). Mice were either challenged with 1×, 12.5×, or 50× the MLD$_{50}$ of VV-WR, 4 days after vaccination with either MVA-BN®, or Elstree, or Dryvax®. In additional groups, mice have been challenged with 1×, 12.5×, or 50× the MLD$_{50}$ of VV-WR, 3 days after vaccination with MVA-BN®; or mice have been challenged with 1× the MLD$_{50}$ of VV-WR, 2 days after vaccination with MVA-BN®. In control groups, mice have been challenged with 1×, 12.5×, or 50× the MLD$_{50}$ of VV-WR, without prior vaccination. Control animals receiving the 1× and 12.5×, or 50× the MLD$_{50}$ of VV-WR were sacrificed 5 or 4 days after challenge, respectively, in case body weight loss exceeded 20% from initial body weight, or in case the animals suffered from dyspnea. This was done to reduce suffering.

TABLE 1

Dose and challenge regimen of mice used to investigate the onset of MVA-BN® protection

| Group | Vaccination | Sample Size | Challenge Dose (x the MLD$_{50}$ of VV-WR) | Time between vaccination and challenge |
|---|---|---|---|---|
| 1 | Saline | 5 | 1x | 4 days |
| 2 | Saline | 5 | 12.5x | 4 days |
| 3 | Saline | 5 | 50x | 4 days |
| 4 | MVA-BN® | 5 | 1x | 4 days |
| 5 | MVA-BN® | 5 | 12.5x | 4 days |
| 6 | MVA-BN® | 5 | 50x | 4 days |
| 7 | MVA-BN® | 5 | 1x | 3 days |
| 8 | MVA-BN® | 5 | 12.5x | 3 days |
| 9 | MVA-BN® | 5 | 50x | 3 days |
| 10 | MVA-BN® | 5 | 1x | 2 days |
| 11 | Dryvax® | 5 | 1x | 4 days |
| 12 | Dryvax® | 5 | 12.5x | 4 days |
| 14 | Dryvax® | 5 | 50x | 4 days |
| 15 | Elstree | 5 | 1x | 4 days |
| 16 | Elstree | 5 | 12.5x | 4 days |
| 17 | Elstree | 5 | 50x | 4 days |

Justification of Group Size

The primary endpoint of the study was efficacy, determined by the level of protection at day 4 or 5 following intranasal challenge with VV-WR. Based on previous preclinical experience, it was assumed that following challenge at least 95% of the vaccinated group is protected, whereas no more than 5% of the placebo treated group is protected. Using Fisher's Exact test, a group size of 5 versus 5 is sufficient to demonstrate a significant difference at the two-sided significance level $\alpha=0.05$ with power greater than 80%.

Administration of Test Articles for Vaccination

Vaccinations were performed in a microbiological safety cabinet (SW 1000 40/class II, Holten Lamin Air). Mice were vaccinated with 200 µl of MVA-BN® (1×10$^8$ TCID$_{50}$/ml) or Saline control (200 µl PBS) via the subcutaneous route in the skin wrinkle of the hind leg using a 1 ml 29G tuberculin insulin syringe (Terumo). Mice receiving Elstree and Dryvax® were anaesthetized before the scarification of the tail: a fresh mixture containing 75 mg Ketamine, 5 mg Xylazine and water was prepared, and 80 µl of the anaesthetic was administered via the subcutaneous route using a 1 ml 27 G insulin syringe. All mice belonging to the same cage were anaesthetized before administering the vaccine. Subsequently, 2.5 µl or 8 µl of Elstree or Dryvax®, respectively, was applied via tail scarification.

Lung Challenge Model

The test article (i.e. VV-WR) was administered via the intranasal route in anaesthetised mice in a microbiological safety cabinet (SW 1000 40/class II, Holten Lamin Air).

A fresh mixture of 75 mg Ketamine, 5 mg Xylazine in water was prepared as anaesthetic. 80 µl of the anaesthetic was administered via the subcutaneous route using a 1 ml 29 G insulin syringe. All mice belonging to the same cage were anaesthetized before administering the VV-WR test article.

Intranasal challenge was performed in a microbiological safety cabinet (SW 1000 40/class II, Holten Lamin Air). The challenge virus working dilution was removed from the ice and mixed by gently vortexing for a few seconds. 50 µl of the diluted VV-WR test article was measured using a 100 µl pipette. Each anaesthetized mouse was held by the skin/fur on the back of the neck and the body was supported in the palm of the same hand. The test item was slowly added into a single nostril of each mouse. Each mouse was held as described above until the gasping ceased.

Prior to challenge (day 0), and daily following challenge, animals were observed to monitor any signs of ill health. Body weight was measured prior to challenge (day 0), and daily post challenge, until the day of necropsy to monitor the development of disease.

The saline group that received 50× the $MLD_{50}$ of VV-WR exceeded the body weight cut off set by the Dyreforsøgstilsyn and was sacrificed on day 4 post challenge. The saline groups that received 1× or 12.5× the $MLD_{50}$ of VV-WR exceeded the body weight cut off set by the Dyreforsøgstilsyn and were sacrificed on day 5 post challenge. Vaccinated animals challenged with 1× the $MLD_{50}$ of VV-WR were sacrificed on day 5 post challenge, whereas MVA-BN®-vaccinated animals challenged with 12.5× or 50× the $MLD_{50}$ of VV-WR were sacrificed latest on day 8 post challenge.

Lungs were removed and the total amount of virus in the lungs was determined using a standard plaque assay on Vero cells. Animals were considered completely protected when lung titers were below $5 \times 10^3$ pfu, the lowest titer detectable using our method of virus titration on Vero cells.

4. Results and Discussion

Changes in Body Weight

The effect of vaccination with different smallpox vaccines on the body weight, following a challenge 4 days later (i.e., 4 days after vaccination) with 1× the $MLD_{50}$ of vaccinia virus strain Western Reserve (VV-WR) was investigated in some groups of this study. As shown in FIG. 1, body weight loss in the group of non-vaccinated (Saline control) mice challenged with 1× the $MLD_{50}$ of VV-WR was first detectable 3 days after the challenge. The body weight continued to drop until sacrifice on day 5 to an average of 20.9% below the average initial body weight. A similar body weight loss was detected in the groups vaccinated with Elstree or Dryvax® 4 days prior to challenge with VV-WR; the average body weight on day of sacrifice was either 23.2% or 21.1% below the initial average body weight in these groups, respectively. In the group vaccinated with MVA-BN® 2 days prior to challenge with VV-WR, the first body weight loss (about 4% from average initial body weight) was detected 2 days post challenge. The average body weight continued to drop in this group until day 4 post challenge, with an average body weight of 17.6% below the initial one. On day 5 post challenge, the average body weight did not continue to drop and was 16.7% below the initial average body weight. In the group vaccinated with MVA-BN® 3 days prior to challenge, only a small drop in body weight was detected, starting on day 3 post challenge and being maximally 4.2% below the initial body weight on day 4 post challenge. In this group, the body weight recovered on day 5 to initial values. The group of mice vaccinated with MVA-BN® 4 days prior to challenge did not show any body weight loss following a challenge with 1× the $MLD_{50}$ of VV-WR.

In a second set of groups, mice were challenged with 12.5× the $MLD_{50}$ of VV-WR and body weight of the mice were again monitored prior to challenge and then daily post challenge. As shown in FIG. 2, body weight loss in the group of non-vaccinated (Saline control) mice was first detectable 2 days after the challenge. The body weight continued to drop until sacrifice on day 5 to an average of 23.3% below the average initial body weight. Thus, the body weight loss was detectable one day earlier than in the non-vaccinated group challenged with 1× the $MLD_{50}$ of VV-WR, and was more pronounced on the day of sacrifice (see FIG. 1). A body weight loss similar to that shown by the non-vaccinated mice was detected in the groups vaccinated with Elstree or Dryvax® 4 days prior to challenge with VV-WR. In the group vaccinated with MVA-BN® 3 days prior to challenge with VV-WR, a first small body weight loss (about 1.7% from average initial body weight) was detected 2 days post challenge. The average body weight continued to drop in this group until day 4 post challenge, with an average body weight of 16.1% below the initial one. Thereafter, the average body weight started to recover in this group, and on day 8 post challenge an average body weight that was 2.3% below the average initial body weight was detected. In the group of mice vaccinated with MVA-BN® 4 days prior to challenge, an average body weight loss of 10.8% compared to the average initial body weight was detected on day 2 post challenge. A maximal average body weight loss of 13.8% was detected on day 3 post challenge. Recovery of body weight was detected on the subsequent days with a similar average body weight detected 8 days post challenge than that detected prior to challenge.

Figure 3:
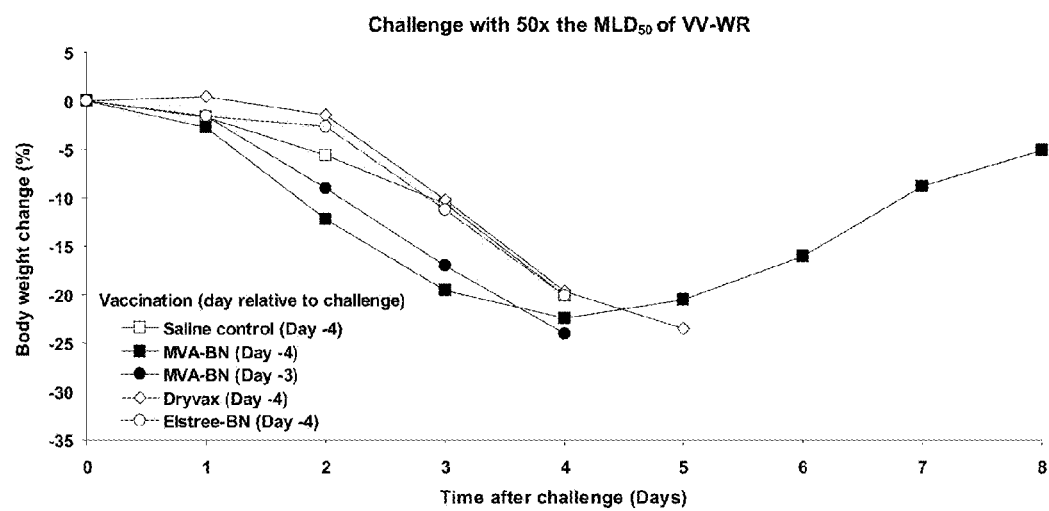
FIG. 3. Changes in body weight of differently vaccinated mice following an intranasal challenge with 50× the MLD$_{50}$ of VV-WR. BALB/c mice were vaccinated subcutaneously with MVA-BN® or saline (PBS) or by scarification with Elstree, Dryvax®. Mice were treated with Saline (PBS) or Elstree, Dryvax 4 days, or with MVA-BN® 3 days prior to challenge with $4\times10^6$ TCID$_{50}$/ml, $1\times10^7$ TCID$_{50}$/ml, or $4\times10^7$ TCID$_{50}$/ml VV-WR per mouse. Body weight was measured prior to challenge (day 0) and then daily post challenge at the same time each day. The graph represents the average body weight changes per group over time using normalized (day 0 as baseline value) individual values.

In a third set of groups, mice were challenged with 50× the $MLD_{50}$ of VV-WR and the body weight of the mice was again monitored prior to challenge and then daily post challenge. As shown in FIG. 3, a first body weight loss in the group of non-vaccinated (Saline control) mice was already detectable 1 day post challenge. The average body weight continued to drop until sacrifice on day 4 to 20.1% below the average initial body weight. Thus, the body weight loss was detectable 2 days or 1 day earlier than that in the non-vaccinated group challenged with 1× or 12.5× the $MLD_{50}$ of VV-WR, respectively. The body weight loss in the groups vaccinated with Elstree or Dryvax® started to be detectable 2 days post challenge, and by day 4 post challenge the mice in these groups revealed an average body weight loss of 20.1% or 19.7% from the initial body weight, respectively. In the group vaccinated with MVA-BN® 3 days prior to challenge with VV-WR, the first body weight loss (about 1.6% from average initial body weight) was detected the first day post challenge. The average body weight continued to drop in this group until sacrifice on day 4 post challenge, with an average body weight of 24.0% below the initial one. In the group of mice vaccinated with MVA-BN® 4 days prior to challenge, a first body weight loss was detectable on the first day post challenge, and the average body weight continued to drop to 22.5% below the average initial body weight on day 4 post challenge. Recovery of body weight was detected on subsequent days, and on day 8 post challenge an average body weight was detected that was 5.1% below the average initial one.

Lung Titers

After death or sacrifice of mice, lungs were removed and the total amount of virus in this tissue was determined using a standard plaque assay on Vero cells. Animals were considered completely protected when lung titers were below log 10 3.69 ($5 \times 10^3$ pfu), the lowest titer detectable using our method of virus titration on Vero cells.

Figure 4:
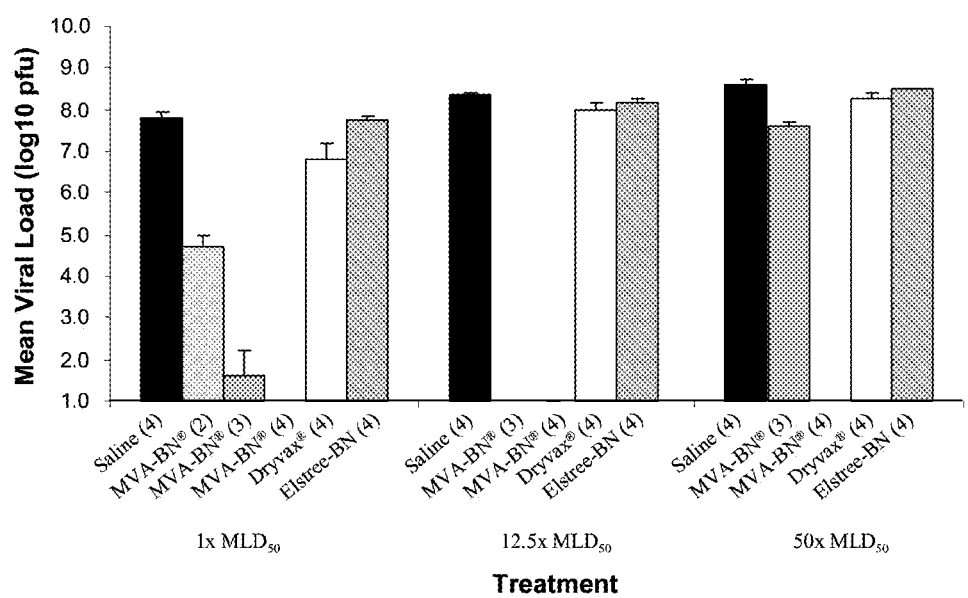
FIG. 4. Titers of the VV within the lungs following challenge. BALB/c mice were vaccinated with a single administration of MVA-BN®, Elstree-BN, Dryvax, or treated with Saline (PBS). On days 2, 3 or 4 (as indicated in brackets) post-vaccination, mice were challenged with either 1×, 12.5×, or 50×MLD$_{50}$ of VV-WR per mouse. The titers of VV-WR in the lungs were determined by a standard plaque assay 4 to 8 days post challenge and expressed at the man log$_{10}$ together with SEM.

In a first set of groups, mice challenged with 1× the $MLD_{50}$ of VV-WR were compared. As shown in FIG. 4, non-vaccinated mice revealed an average virus load of log 10 7.81. Mice vaccinated with Elstree or Dryvax® 4 days prior to challenge revealed an average lung virus load of log 10 7.75 and log 10 6.68. Thus, the Elstree vaccinated mice were unable, and the Dryvax® vaccinated mice were only to some degree able, to prevent lung viral infection. On the other hand, in the group of mice vaccinated with MVA-BN® 4 days prior to challenge, no lung viral titers could be detected and these mice are thus completely protected from viral infection following intranasal challenge with 1× the $MLD_{50}$ of VV-WR. Shortening the interval between vaccination with MVA-BN® and challenge with VV-WR from 4 to 3 or 2 days, increased the number of virus-positive lungs per group to 1 out of 5, or 4 out of 5, with average lung viral titers of log 10 3.77 or log 10 4.68, respectively.

In a second set of groups, mice challenged with 12.5× the $MLD_{50}$ of VV-WR were compared. As shown in FIG. 4, non-vaccinated mice revealed an average virus load of log 10 8.38. Mice vaccinated with Elstree or Dryvax® 4 days prior to challenge, revealed an average lung virus load of log 10 8.17 and log 10 8.00. Thus, the Elstree and the Dryvax® vaccinated mice were unable to prevent lung viral infection. On the other hand, in the group of mice vaccinated with MVA-BN® 4 or 3 days prior to challenge, no lung viral titers could be detected and these mice are thus completely protected from viral infection following intranasal challenge with 12.5× the $MLD_{50}$ of VV-WR.

In a third set of groups, mice challenged with 50× the $MLD_{50}$ of VV-WR were compared. As shown in FIG. 4, non-vaccinated mice revealed an average virus load of log 10 8.59. Mice vaccinated with Elstree or Dryvax® 4 days prior to challenge revealed an average lung virus load of log 10 8.49 and log 10 8.25. Thus, the Elstree and the Dryvax® vaccinated mice were unable to prevent lung viral infection. On the other hand, in the group of mice vaccinated with MVA-BN®, no lung viral titers was detected when vaccination was administered 4 days prior to challenge. Consequently, these mice are protected from viral infection following intranasal challenge with 50× the $MLD_{50}$ of VV-WR. In the group of mice in which a 3 day interval between MVA-BN® vaccination and challenge with VV-WR was applied an average lung viral load of log 10 7.63 was determined. Thus, this group is only to some degree protected from viral infection.

5. Conclusions

In the present study, described as Example 1, recovery from body weight loss as well as viral lung titers have been determined to indicate "protection" from a lethal intranasal challenge with VV-WR.

Control animals challenged with 1×, 12.5×, or 50× the $MLD_{50}$ of VV-WR revealed a continuous loss of body weight and had a high viral load in the lungs post-mortem (the higher the challenge dose, the higher the viral load detected in the lungs). Thus, these mice were unable to control the infection.

The smallpox vaccine candidate IMVAMUNE™ (MVA-BN®) was able to protect against an intranasal challenge with up to 50× the $MLD_{50}$ of VV-WR. This protection was associated with recovery of body weight after initial body weight loss and was also associated with lack of virus in the lungs. The higher the challenge dose of VV-WR, the longer the post challenge period required for body weight recovery in the mice vaccinated 4 days prior to the challenge with MVA-BN®. Indeed, when challenged with 12.5× the $MLD_{50}$ of VV-WR body weight recovery was detected on day 4 post challenge, whereas body weight recovery was detected on day 5 post challenge when mice have been challenged with 50× the $MLD_{50}$ of VV-WR. In addition, this study clearly revealed that the time interval between vaccination of mice with MVA-BN® and challenge with 1× the $MLD_{50}$ of VV-WR can be reduced to 2 days, a time interval that is sufficient to enable stabilization of body weight and to obtain reduced lung viral titers following challenge of mice with 1× the $MLD_{50}$ of VV-WR. Furthermore, increasing the challenge doses resulted in an extension in the time interval between vaccination with MVA-BN® and challenge that is required to obtain protection from the lethal challenge. Accordingly, in case of challenge with 50× the $MLD_{50}$ of VV-WR a 3 day interval was not sufficient, whereas following challenge with 12.5× the $MLD_{50}$ of VV-WR a 3 day interval between vaccination and challenge was sufficient to obtain protection.

In contrast to MVA-BN®, the first and second generation smallpox vaccines Dryvax® and Elstree, respectively, were unable to protect against an intranasal challenge with up to 50× the $MLD_{50}$ of VV-WR when administered 4 days prior to the challenge. The reason for this difference might be due to the different routes of administration: MVA-BN® was administered to mice (and is administered in clinical trials to humans) subcutaneously, whereas Elstree and Dryvax® was administered to mice (and is administered in clinical trials to humans) via scarification.

In summary, the study described in Example 1 clearly demonstrates the superiority of MVA-BN® over Elstree and Dryvax® with regard to onset of immune protection.

Example 2

Onset of Protection in MVA-BN®, Elstree, or Dryvax® Vaccinated Mice Challenged with 1×, 12.5×, or 50× the $MLD_{50}$ of Vaccinia Virus VV-Western Reserve (VV-WR) on Days 2 Through 14 Post-Vaccination: Assessment by Body Weight, Lung Titers, and Specific-IgG Titers As described below, Example 2 summarises a series of studies that have investigated the onset of protection afforded by various smallpox vaccines, including MVA-BN®, using the VV challenge model in mice. as assessed by measurements of vaccinia-specific IgG titers, in addition to body weight and lung titers.

1. Viruses and Controls

All viruses and controls were as described above for Example 1.

2. Methods and Experimental Design

The Test System was as described above in Example 1.

Vaccination and Challenge Schedule

As illustrated in Table 2, mice (n=5/group) were challenged with either 1×, 12.5× or 50× the $MLD_{50}$ of VV-WR either 7 or 14 days after a single subcutaneous (s.c.) administration of either Saline (s.c.) or MVA-BN®. As a comparison to other traditional smallpox vaccines, other groups were vaccinated with either Dryvax® or Elstree-BN by tail scarification. Control animals receiving VV-WR challenge were sacrificed 4 or 5 days after challenge when the mean body weight loss exceeded 20% from initial body weight, or when the animals suffered from dyspnea.

TABLE 2

Dose and challenge regimen of mice used to investigate the onset of MVA-BN® protection.

| Treatment | Dose ($TCID_{50}$) | VV-WR Challenge Dose ($MLD_{50}$) | Timing of VV-WR challenge (Days post-Vaccination) 7 | 14 |
|---|---|---|---|---|
| Saline | 0 | 1x | X | X |
| | | 12.5x | | |
| | | 50x | X | X |
| MVA-BN® | 1 × $10^8$ | 1x | X | X |
| | | 12.5x | | |
| | | 50x | X | X |
| Dryvax | 2.5 × $10^5$ | 1x | X | X |
| | | 12.5x | | |
| | | 50x | X | X |
| Elstree-BN | 2.5 × $10^5$ | 1x | X | X |
| | | 12.5x | | |
| | | 50x | X | X |

Justification of Group Size Based on previous preclinical experience it was assumed that following challenge at least 95% of the vaccinated group was protected whereas no more than 5% of the Saline treated group were protected. Based on Fisher's Exact test a group size of 5 versus 5 is sufficient to demonstrate a significant difference at the two-sided significance level $\alpha=0.05$ with power greater than 80%.

In-Life Evaluations and Necropsy Preparations

Clinical Signs

Animals were monitored daily for signs of illness; each animal was recorded (at the same time each day) as healthy, sick or dead prior to VV-WR challenge (Day 0) and daily following challenge. Body weight was measured prior to VV-WR challenge (Day 0) and daily post challenge, until the day of necropsy to monitor for development of disease.

Blood Collection

Blood (100-150 µl) from the individual mice was collected prior to the first vaccine or saline administration and at varying intervals throughout the respective study prior to and post-challenge with VV-WR. Respective study sera sample time points are indicated in the results section. The blood was collected, and separated using Microtainer™ serum separation tubes according to the manufacturer's instructions (Becton Dickinson). The tubes containing sera from each mouse were labelled and stored below −15° C. until required for ELISA analysis to determine vaccinia specific IgG titers.

Lung Preparation

Lungs were harvested at the end of the observation period post-challenge and placed into 5 ml of DMEM tissue culture medium (Invitrogen) supplemented with 100 U penicillin/ 100 µg/ml streptomycin (Sigma) and 2% foetal bovine serum, FBS (PAA). The tubes containing lungs from each mouse were labelled using appropriate computer printed adhesive labels and stored below −15° C. until required for use in a Vero cell plaque assay to determine VV-WR viral lung titer.

Vaccinia-Specific ELISA

Vaccinia-specific IgG ELISA titers were determined from serum samples as described in SOP/PRE/005. The antibody titers (log 10) were calculated by linear regression (OD on the y-axis and log of the sera dilution on the x-axis) and defined as the serum dilution that resulted in an optical density (OD 492 nm) of 0.3. The regression analysis was performed using the Magread Macro software as described in SOP/IMM/028. Assay acceptance criteria of OD<0.20 and OD>1.0 have been defined for the negative and positive samples respectively. The mean antibody titers were illustrated as Geometric Mean Titer (GMT), together with the SEM.

Titration of VV-WR from Lung Samples on Vero Cells

VV-WR viral titers from the prepared lungs were determined by virus titration on Vero cells as described in SOP/ PRE/001. Plaque numbers were counted using photographic images of the plates and a computerised system (Zeiss Imaging System). The resulting plaque counting raw data were automatically inserted into an Excel spread sheet that was then used to calculate viral titer as Log 10 PFU (plaque forming units). For summarizing the generated data, the calculated viral titers were manually inserted into a further (Excel) template. For assay acceptance, the positive control sample had to generate plaque numbers150/well in the 6400× dilution. The detection limit of the assay was Log 10 3.69.

Data Handling

Microsoft Excel 2000 was used to generate templates for data documentation. Appropriate raw data was entered manually into the printed templates and then attached to laboratory notebooks. Manually entered data was then transferred into Excel for analysis (e.g. calculation of average values, SEMs and GMTs).

Data Evaluation

Body weight (in grams) was monitored prior to challenge (Day 0) and daily post challenge. Changes in body weight for the post-challenge period were calculated in % using Microsoft Excel for the individual mice. The average change for each group +/− the standard error was calculated for each time point post challenge. Lung VV-WR and sera vaccinia IgG titers (as $\log_{10}$ titers) were expressed as average +/− standard error per test group. Body weight and lung titer data sets were illustrated graphically using Microsoft Excel.

Statistical analysis was performed using StatXact 6.1 from Cytel Software and JMP 6.0.0 from SAS. A statistical significance is defined as $p<0.05$. For the non-parametric multiple comparison tests, a simple Bonferroni correction was made (significance was claimed if $p<0.05/N$ where N was the number of comparisons).

3. Results and Discussion

Vaccinia-Specific Antibody Induction

Although previous studies, including Example 1, have shown that mice vaccinated with MVA-BN® generate an equivalent immune response to traditional smallpox vaccines, time course studies have revealed that the immune response is induced faster following MVA-BN®, compared to the traditional vaccines. However, as has previously been reported, there is a relatively high failure rate (20-30%) of administering traditional smallpox vaccines by tail scarification in mice. In contrast, there is a 100% sera-conversion by ELISA in the mice vaccinated with MVA-BN® at the optimal dose (1×108 TCID50). Therefore in an initial analysis, the antibody responses induced by the various smallpox vaccines were compared for up to 22 days post vaccination, and to overcome the problem of vaccine take failures, 5 animals vaccinated with MVA-BN® were compared (at certain time points) to groups sizes of 25 and 21 for Elstree-BN and Dryvax® respectively.

Figure 5:
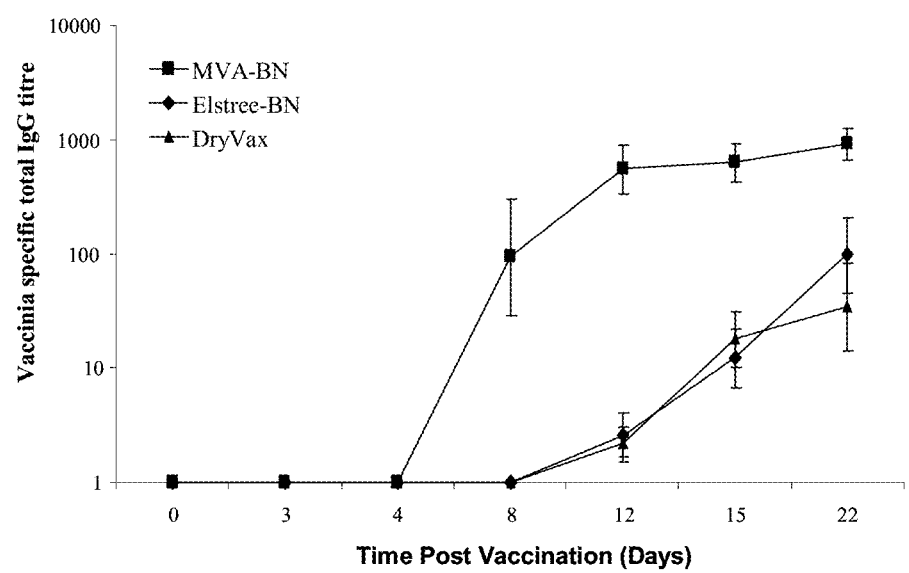
FIG. 5. Comparison of antibody responses induced by MVA-BN®, Elstree-BN or Dryvax® immunizations. Balb/c mice were vaccinated with a single administration of MVA-BN®, Elstree-BN or Dryvax. Sera samples prepared on days 0 (pre-vaccination), 3, 4, 8, 12, 15 and 22 were analyzed by ELISA for vaccinia-specific IgG titers. The titers have been plotted as GMT together with the SEM.

As illustrated in FIG. 5, following the vaccination with MVA-BN®, a detectable antibody titer could be measured in the majority of the animals (4 out of 5 mice) by day 8 post vaccination, with a GMT of 94. By day 12 there was a 100% sera-conversion and the GMT titer increased to 548 that continued to rise steadily until day 22 post vaccination (GMT 912). In contrast, no mice vaccinated with either Dryvax® or Elstree-BN had sera-converted by day 8 post vaccinated and only moderate antibody responses could be detected in a minority of animals at day 12 and 15 post vaccination. It is difficult to completely assess which animals failed to induce immune responses, due to the failure in administering the vaccines, especially at the earlier time points. However, of the 11 animals vaccinated with Elstree-BN that had sera-converted by day 22, none had sera-converted on day 8; only 3 had sera converted by day 12, which rose to a total of 7 by day 15 (an additional 4 mice) and the remaining 4 animals only sera-converted on day 22 post vaccination. Similarly, of the 7 animals vaccinated with Dryvax® that had sera-converted by day 22, none had sera-converted on day 8; only 2 had sera converted by day 12, which rose to a total of 5 by day 15 (an additional 3 mice) and the remaining 2 animals only sera-converted on day 22 post vaccination. Thus, seroconversions are induced within 8-10 days following vaccination with MVA-BN®, while traditional vaccines take 12-22 days to induce a similar response in mice.

Challenge of Animals within Two Weeks Post-Vaccination

The experiment described in Example 1 (see above) demonstrated the superiority of MVA-BN® over traditional vaccines Elstree and Dryvax® in affording protection from viral challenges given at days 2, 3, or 4 post-vaccination. To further identify the putative time following vaccination when the traditional smallpox vaccines would induce protection in the same manner as MVA-BN® vaccinated animals, additional studies were performed whereby vaccinated animals were challenged with either a low ($1 \times MLD_{50}$) or standard ($50 \times MLD_{50}$) challenge dose at 7 or 14 days post vaccination. As expected, the placebo treated groups had a mean body weight loss of −24% 5 days post challenge ($1 \times MLD_{50}$), with a mean VV titer in the lung of log 10 7.62 pfu (FIG. 6A). Both Elstree-BN and Dryvax® induced a partial protection after 7 days when challenged with the low dose VV-WR, with a 20% (⅕ animals) and 60% (⅗) efficacy respectively (FIG. 6A). Indeed, 1 and 2 of the Elstree-BN and Dryvax® animals had to be sacrificed on day 4 post challenge, due to a >20% weight loss and in the Dryvax® group these animals represented the major reason for the mean weight loss on day 4 post challenge (FIG. 6A). By 14 days post vaccination, both Elstree-BN and Dryvax® had induced a good protection, as both groups of animals lost a minimal amount of mean body weight, although one animal in each group did have a positive titer in the lungs. (Elstree-BN, log 10 7.56 pfu and Dryvax®, log 10 3.70 pfu; FIG. 6A).

Figure 6:
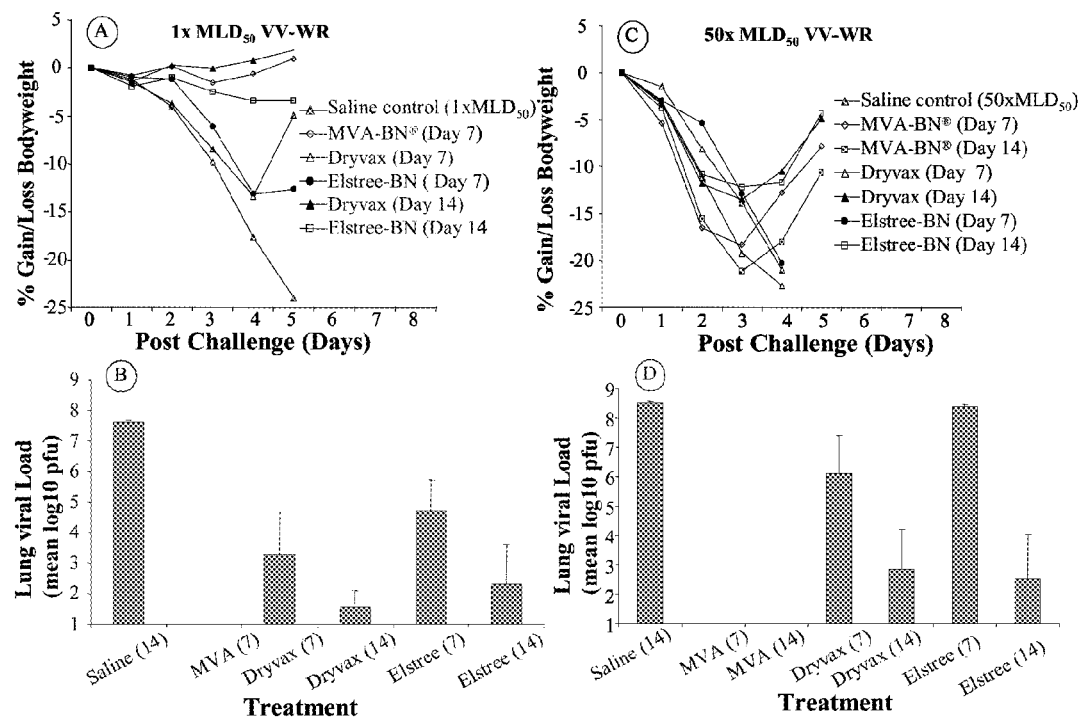
FIG. 6 A-D. Body weight loss and lung VV-WR titers in mice challenged with either 1× (A & B) or 50× (C & D) MLD$_{50}$ VV-WR on days 7 or 14 post-vaccination. Mice were vaccinated with either IMVAMUNE® (s.c.), Elstree-BN (scarification) or Dryvax® (scarification) and then challenged with either 1× or 50×MLD$_{50}$ VV-WR on day 7 or 14 post vaccination. Body weights were monitored and the animals sacrificed day 5 post challenge and the titers of VV-WR in the lungs were determined by a standard plaque assay.

As illustrated in FIG. 6C, the group of placebo treated animals challenged ($50 \times MLD_{50}$) 14 days post vaccination had a mean body weight loss of 21% by day 4 post challenge at which time point they were sacrificed due to the ethical constraints (weight loss not to exceed 20%). At this time point the placebo animals recorded a mean VV-WR titer of log 10 8.49 pfu in their lungs (FIG. 6D). In contrast, all the animals vaccinated once with MVA-BN® were fully protected 7 or 14 days post vaccination, as these animals had completely cleared the challenge VV from their lungs 5 days post challenge (FIG. 6B and FIG. 6D). Moreover, all MVA-BN® vaccinated animals experienced a weight loss (mean −18.38 to −21.23%) 3 days following the challenge that appeared to be independent of when they had been vaccinated (i.e. 7 or 14 days before challenge), although all animals showed signs of recovery by the end of the post challenge observation period (FIG. 6). The animals vaccinated with either Elstree-BN or Dryvax® were completely not protected when challenged 7 days later. Indeed, all vaccinated animals failed to last the full observation period and like the placebo treated animals had to be sacrificed 4 days post challenge, due to mean weight losses of −20.30% and −22.69% for the Elstree-BN and Dryvax® vaccinated animals respectively. These animals had clearly succumbed to the VV-WR challenge, as mean viral titers of log 10 8.37 pfu (Elstree-BN) and log 10 7.38 pfu (Dryvax®) were recovered from their lungs 4 days post challenge (FIG. 6). However, both traditional smallpox vaccines induced almost a complete protection 14 days following vaccination, as ⅘ animals were protected in both the Elstree-BN and Dryvax® treated groups, as judged by the clearance of the challenge virus from their lungs 5 days post challenge (FIG. 6). This partial protection was also reflected in the recorded body weight losses, with maximal mean weight losses on day 3 post challenge of −12.19% and −13.49% in the Elstree-BN and Dryvax® treated groups respectively (FIG. 6).

MVA-Specific Antibody Titer and Lung VV-WR Titer

Antibodies are not detected in MVA-BN®-vaccinated mice by ELISA until day 7 to day 10 post vaccination, and even later for mice vaccinated with traditional smallpox vaccines. Therefore, in an attempt to better understand the protective mechanism observed, particularly in the MVA-BN® treated animals, blood was analyzed after the challenge period for total IgG titers specific against vaccinia by ELISA.

No antibody titers could be detected in the placebo treated animals post challenge, clearly indicating that challenge with VV-WR at any of the doses investigated, did not raise a detectable immune response to VV (Table 3). In the animals vaccinated with MVA-BN® and challenged 3 days later with $50 \times MLD_{50}$ VV-WR, no antibodies could be detected by ELISA and as reported above, all animals were not protected with a mean VV titer in the lungs that was equivalent to placebo treated animals (Table 3). However, 4 days after vaccination with MVA-BN® all animals had a detectable antibody response, with a GMT of 597 post challenge and all animals were fully protected from the same lethal challenge of VV-WR (Table 3).

While all MVA-BN® vaccinated animals were fully protected from 4 days post treatment, interestingly the GMT increased post challenge the longer between vaccination and when the challenge took place; with a GMT of 705 and 1516 after challenge on day 7 and 14 respectively (Table 3). Similarly, 7 days after vaccination with either Elstree-BN or Dryvax® the animals had no detectable antibodies post challenge ($50 \times MLD_{50}$) and all animals succumbed to the challenge with high VV titers in the lungs (Table 3). Two weeks post vaccination with Elstree-BN, only one animal had a VV titer in the lung (log 10 8.52 pfu) and this is the only animal that had no detectable antibodies following challenge. The remaining 4 protected animals all had detectable antibodies following challenge, with a GMT of 282. Similarly, the 4 animals vaccinated with Dryvax® that were protected when challenged ($50 \times MLD_{50}$) 14 days following vaccination also all had a detectable antibody response post challenge. Again the one non-protected animal had a lung titer of log 10 7.87 and had no detectable antibodies following challenge. Interestingly however, all the MVA-BN® vaccinated animal that were challenged ($1 \times MLD_{50}$) 2 days post treatment had detectable antibodies (GMT of 106) following challenge and were un-protected with a mean log 10 titer of 4.68. However, even in this case the viral load in the lungs was lower than expected, indicating that the MVA-BN® had an effect even after two days post vaccination. Indeed, there was a significant ($p<5\times10^{-9}$) negative correlation between the induction of antibodies post challenge to the VV-WR titers in the lungs when a Cohen Kappa, test of agreement was performed on all values (including the 2 days post MVA-BN® group).

TABLE 3

Immunogenicty and efficacy of MVA-BN®, Elstree-BN and Dryvax®

| Treatment[a] | Vaccination Dose ($TCID_{50}$) | Day of Challenge (post vaccination) | Total IgG titer post challenge $(GMT)^b$ | Lung viral load at sacrifice $(log10)^c$ |
|---|---|---|---|---|
| Saline | — | 4 | 1 | 8.59 +/− 0.14 |
|  |  | 14 | 1 | 8.49 +/− 0.08 |
| MVA-BN® | $1 \times 10^8$ | 3 | 1 | 7.63 +/− 0.08$^{e**}$ |
|  |  | 4 | 597** | 1.00 +/− 0$^{d**}$ |
|  |  | 7 | 705** | 1.00 +/− 0** |
|  |  | 14 | 1516** | 1.00 +/− 0** |
| Elstree-BN | $2.5 \times 10^5$ | 4 | 1 | 8.49 +/− 0.03 |
|  |  | 7 | 1 | 8.37 +/− 0.08 |
|  |  | 14 | 282* | 2.50 +/− 1.50* |

TABLE 3-continued

Immunogenicty and efficacy of MVA-BN®,
Elstree-BN and Dryvax®

| Treatment[a] | Vaccination Dose (TCID$_{50}$) | Day of Challenge (post vaccination) | Total IgG titer post challenge (GMT)[b] | Lung viral load at sacrifice (log10)[c] |
|---|---|---|---|---|
| Dryvax® | 2.5 × 10$^5$ | 4 | 1 | 8.25 +/− 0.17 |
| | | 7 | 1 | 6.10 +/− 1.30** |
| | | 14 | 84* | 2.85 +/− 1.34** | vaccinated mice challenged with VV WR (50x MLD$_{50}$).
Total IgG antibody titers are expressed as GMT. Lung titers are expressed as log10 +/− the standard deviation from the mean. Statistical significance from the saline control is indicated by * and ** for p < 0.05 and 0.01 respectively.
[a]Mice (n = 5) were immunized with the vaccines below and challenged via the intranasal route on days 3, 4, 7 or 14 post vaccination with 2 × 10$^6$ TCID$_{50}$ (50x MLD$_{50}$).
[b]Total IgG titers of 1 were assigned when the absorbance at a 1:50 starting dilution was below 0.3.
[c]Control mice were sacrificed on day 4 post challenge. Vaccinated mice were sacrificed on day 4 or 5 post challenge. Lung viral load determined by plaque assay.
[d]Mice were sacrificed on day 8 post challenge.
[e]Lung titers were statistically different from MVA-BN vaccinated groups with no virus detected in the lungs (p < 0.01)

4. Conclusions

The studies described above have demonstrated that a single vaccination with MVA-BN® induces a detectable antibody response within the first week in the majority of animals, whereas traditional vaccines, based on replicating VV, actually take longer (up to 22 days) to induce the equivalent responses in mice, in non-human primates (Stittelaar et. al. 2005, J. Virol. 2005 79:7845-51), and in an in-house Phase I clinical study. The results described in the Examples confirmed that MVA-BN® induced sera-conversion by 7 to 14 days post vaccination, whereas traditional smallpox vaccines peak response was 22 days after vaccination. The induction of immunity in animals following vaccination with Dryvax® or Elstree-BN parallels the induction of the vaccine take, as sera-conversion only begins to become noticeable 12 days post vaccination, after the formation of the pustule following scarification; also, the majority of the animals require between 14 to 22 days to sera-convert, after the formation of the scab. Indeed, this also appears to be the case for people vaccinated with Dryvax®, as others have reported that the peak antibody response was 22 days post vaccination in a clinical setting (Frey et al., 2002, N Engl J Med 346:1275-1280).

It could be argued that this is an inappropriate comparison as MVA-BN® is given at a 400× higher dose than the traditional smallpox vaccines Elstree and Dryvax®. However, these studies were designed to compare the vaccine regimes recommended for people (and shown optimal for mice), both in terms of dose and route of administration. While higher doses of Dryvax® could change the dynamics of the immune response, this would only be feasible by changing the route of administration (s.c. or intramuscular), something which would raise severe safety concerns, even for healthy people. Of note, by 22 days after vaccination, the immune responses induced by both MVA-BN® and Dryvax® are equivalent in mice, non-human primates (Stittelaar et. al. 2005, J Virol. 2005 79:7845-51) and people. This has also been shown for other MVA strains in comparison to Dryvax® in animal models, including non-human primates (Wyatt et al., 2004, PNAS. 101: 4590-5; Earl et al., 2004, Nature. 428:182-5), suggesting that MVA is not more immunogenic than traditional smallpox vaccines. Therefore, and without being bound by a specific theory, the significantly faster induction of immunity afforded by MVA-BN® compared to Dryvax®, appears to be associated with the dose, the route of administration, or a combination of both.

Indeed, because MVA-BN® fails to replicate, this allows a much higher dose to be administered in one injection. Again without being bound by a specific theory, this allows for a rapid induction of B and T cells, because following a s.c. injection MVA-BN® will travel directly to the draining lymph nodes, the sites of specific immune induction, allowing the direct stimulation of the immune system. In contrast, traditional smallpox vaccines rely on administering a small quantity (dose) of the virus to the skin, which subsequently needs to replicate (leading to the formation of a pustule) in order to stimulate the immune system to induce the same immune response as MVA-BN®; a process that takes longer than a bolus injection of MVA.

This lag in the ability of Dryvax® and Elstree-BN to efficiently stimulate the immune response (in comparison to MVA-BN®), was elegantly demonstrated by the inability of these vaccines to induce protection until 2 weeks post vaccination, whereas MVA-BN® could protect animals within 4 days at the same high challenge dose (50×MLD$_{50}$). Even at lower challenge doses (1× & 12.5×MLD$_{50}$), the traditional smallpox vaccines failed to induce any protection within the first week post vaccination, while MVA-BN® could protect as early as 3 days after vaccination. Even following just 2 days, there were signs that vaccination with MVA-BN® had been beneficial following the low dose challenge (1×MLD$_{50}$) with VV, as there was a reduction in the challenge titers in the lungs compared to placebo treated animals and ⅕ MVA-BN® vaccinated animals was protected.

While antibodies could not be detected prior to a challenge, especially at the earlier time points for the MVA-BN® vaccinated animals (<7 days), these protected animals had sera converted after the challenge. Thus, it is possible that the induction of a specific immunity, rather than the induction of innate (non-specific) mechanisms (e.g. induction of type I interferon, NK cells etc), is a mechanism of protection. Indeed, there was a highly significant negative correlation between VV titers in the lungs following challenge (non-protection) and sera-conversion by ELISA, even for the animals vaccinated with Dryvax®. While only total antibodies were measured in these studies, it has been shown that protection from lethal challenges with VV in mice requires both antibodies and T cells (Wyatt et al., 2004). Given that the ELISA is a more sensitive assay compared to cell based assays for neutralizing antibodies or T cell responses, and that total antibodies correlate to neutralizing antibodies in animals and people vaccinated with MVA-BN® (Stittelaar et. al. 2005, J Virol. 2005 79:7845-51), it appears that sera-conversion by ELISA represents an extremely sensitive assay that is predictive of the induction of a specific immune response. Therefore, while total antibodies measured by ELISA are no more a single correlate of protection, they represent a useful immune parameter that predicts protection following vaccination with either MVA-BN® or traditional smallpox vaccines like Dryvax®.

The data indicate that a factor in the onset of protection is the time required to efficiently prime the immune response, such that it has sufficient time to mature and clear the challenge VV. This was drawn from the relationship between the times required for protection following vaccination with MVA-BN®, to the challenge dose of VV-WR. MVA-BN® vaccinated animals could protect by day 4 post challenge, but not by day 3 at the same challenge dose (50×MLD$_{50}$), whereas at the lower challenge doses (1× & 12×MLD$_{50}$), MVA-BN® could afford protection a day earlier (day 3). The unprotected animals failed to mount an immune response and had not sera-converted after the challenge. Also, the only animals that did sera-convert after the challenge, but failed to induce a full protection 5 days following the challenge, were the animals vaccinated with MVA-BN® and challenged 2 days later. However, given that the mean lung titers were lower than expected from the placebo controls, the results indicate that MVA-BN® did have an effect, but maybe the timing between vaccination and challenge was insufficient to induce an efficient priming of B and T cells to be able to respond and clear the challenge VV within 5 days.

Although post exposure animal models are difficult to develop to mimic the natural situation of variola in people, investigating the onset of protection and comparing this to the gold standard Dryvax®, provides probably the best model to investigate efficacy in a post exposure event. Using this model, Examples 1 and 2 have shown that MVA-BN® (IM-VAMUNE®) is superior at inducing a protective immune response in animal models compared to Dryvax®.

The invention claimed is:

1. A method for inducing a specific immune response against a Variola virus in a human, comprising administering to the human an immunogenic composition comprising an MVA at 7 to 2 days prior to exposure to the Variola virus.

2. The method of claim 1, wherein the MVA is administered in a dose of $10^5$ to $5 \times 10^8$ $TCID_{50}$/ml.

3. The method of claim 2, wherein the MVA is administered in a dose of $10^8$ TCID50/ml.

4. The method of claim 1, wherein the MVA is administered intravenously, intramuscularly, or subcutaneously.

5. The method of claim 1, wherein the MVA is MVA-BN.

6. The method of claim 1, wherein the MVA is a recombinant MVA.

7. The method of claim 6, wherein the MVA comprises at least one heterologous nucleic acid sequence coding for at least one antigenic epitope of an infectious agent.

8. The method of claim 7, wherein the infectious agent is selected from Influenza virus, Flavivirus, Paramyxovirus, Hepatitis virus, human immunodeficiency virus, and viruses causing hemorrhagic fever.

9. The method of claim 7, wherein the infectious agent is *bacillus anthracis*.

10. The method of claim 1, wherein the administration of the immunogenic composition comprising an MVA is at 6 to 2 days prior to exposure to the Variola virus.

11. The method of claim 1, wherein the administration of the immunogenic composition comprising an MVA is at 5 to 2 days prior to exposure to the Variola virus.

12. The method of claim 1, wherein the administration of the immunogenic composition comprising an MVA is at 4 to 2 days prior to exposure to the Variola virus.

13. The method of claim 1, wherein the administration of the immunogenic composition comprising an MVA is at 3 to 2 days prior to exposure to the Variola virus.

14. The method of claim 1, wherein a protective immune response is generated within 7 days of the administration of the immunogenic composition comprising an MVA.

15. The method of claim 1, wherein seroconversion is achieved within 7 days of the administration of the immunogenic composition comprising an MVA.

16. The method of claim 3, wherein the administration of the immunogenic composition comprising an MVA is at 6 to 2 days prior to exposure to the Variola virus.

17. The method of claim 3, wherein the administration of the immunogenic composition comprising an MVA is at 5 to 2 days prior to exposure to the Variola virus.

18. The method of claim 3, wherein the administration of the immunogenic composition comprising an MVA is at 4 to 2 days prior to exposure to the Variola virus.

19. The method of claim 3, wherein the administration of the immunogenic composition comprising an MVA is at 3 to 2 days prior to exposure to the Variola virus.

* * * * *